(12) United States Patent
Johnson et al.

(10) Patent No.: US 9,737,632 B2
(45) Date of Patent: Aug. 22, 2017

(54) FIBER SCAFFOLDS FOR USE CREATING IMPLANTABLE STRUCTURES

(71) Applicant: NANOFIBER SOLUTIONS, INC., Hilliard, OH (US)

(72) Inventors: Jed K. Johnson, London, OH (US); Ross Kayuha, Dublin, OH (US)

(73) Assignee: NANOFIBER SOLUTIONS, INC., Hilliard, OH (US)

( * ) Notice: Subject to any disclaimer, the term of this patent is extended or adjusted under 35 U.S.C. 154(b) by 0 days.

(21) Appl. No.: 14/496,070

(22) Filed: Sep. 25, 2014

(65) Prior Publication Data

US 2015/0086607 A1 Mar. 26, 2015

Related U.S. Application Data

(60) Provisional application No. 61/882,504, filed on Sep. 25, 2013.

(51) Int. Cl.

| | |
|---|---|
| *A61L 27/18* | (2006.01) |
| *A61L 27/54* | (2006.01) |
| *A61L 27/38* | (2006.01) |
| *A61L 27/26* | (2006.01) |
| *A61L 27/58* | (2006.01) |
| *A61L 27/50* | (2006.01) |
| *A61L 27/20* | (2006.01) |
| *A61L 27/14* | (2006.01) |
| *A61L 31/04* | (2006.01) |
| *A61L 31/14* | (2006.01) |
| *A61L 31/16* | (2006.01) |

(52) U.S. Cl.
CPC .......... *A61L 27/18* (2013.01); *A61L 27/14* (2013.01); *A61L 27/20* (2013.01); *A61L 27/26* (2013.01); *A61L 27/38* (2013.01); *A61L 27/3804* (2013.01); *A61L 27/507* (2013.01); *A61L 27/54* (2013.01); *A61L 27/58* (2013.01); *A61L 31/04* (2013.01); *A61L 31/14* (2013.01); *A61L 31/148* (2013.01); *A61L 31/16* (2013.01); *A61L 2300/406* (2013.01); *A61L 2300/41* (2013.01); *A61L 2300/412* (2013.01); *A61L 2300/414* (2013.01); *A61L 2300/416* (2013.01); *A61L 2300/64* (2013.01); *A61L 2400/12* (2013.01); *A61L 2430/02* (2013.01); *A61L 2430/20* (2013.01); *A61L 2430/34* (2013.01); *Y10T 428/249947* (2015.04)

(58) Field of Classification Search
CPC ............ A61L 2400/12; A61L 2430/20; A61L 2430/34; A61L 27/14; A61L 27/507; A61L 27/54; A61L 27/58; A61L 31/14; A61L 31/148; A61L 31/16; Y10T 428/249947

See application file for complete search history.

(56) References Cited

U.S. PATENT DOCUMENTS

| | | |
|---|---|---|
| 4,738,740 A | 4/1988 | Pinchuk et al. |
| 5,258,027 A | 11/1993 | Berghaus |
| 5,628,788 A | 5/1997 | Pinchuk |
| 6,143,022 A | 11/2000 | Shull et al. |
| 7,115,220 B2 | 10/2006 | Dubson et al. |
| 7,220,281 B2 | 5/2007 | Lambrecht et al. |
| 7,390,760 B1 | 6/2008 | Chen et al. |
| 7,413,575 B2 | 8/2008 | Phaneuf et al. |
| 7,490,563 B2 | 2/2009 | Eastin et al. |
| 7,629,030 B2 | 12/2009 | Robertson et al. |
| 7,718,351 B2 | 5/2010 | Ying et al. |
| 7,993,567 B2 | 8/2011 | Scott-Carnell et al. |
| 8,157,722 B2 | 4/2012 | Arnal et al. |
| 8,691,543 B2 | 4/2014 | Gaudette et al. |
| 8,771,582 B2 | 7/2014 | Phaneuf et al. |
| 2002/0142458 A1 | 10/2002 | Williams et al. |
| 2003/0168756 A1* | 9/2003 | Balkus, Jr. ............. B82Y 30/00 264/10 |
| 2003/0226750 A1 | 12/2003 | Fenn |
| 2005/0177249 A1 | 8/2005 | Kladakis et al. |
| 2005/0277985 A1 | 12/2005 | Wert et al. |
| 2006/0085063 A1 | 4/2006 | Shastri et al. |
| 2006/0134157 A1 | 6/2006 | Lehman et al. |
| 2006/0154063 A1 | 7/2006 | Fujihara et al. |
| 2006/0200232 A1 | 9/2006 | Phaneuf et al. |
| 2006/0204539 A1 | 9/2006 | Atala et al. |

(Continued)

FOREIGN PATENT DOCUMENTS

| | | |
|---|---|---|
| CN | 102008755 A | 4/2011 |
| EP | 0416846 A2 | 3/1991 |

(Continued)

OTHER PUBLICATIONS

Meng et al. (Journal of Nanoscience and Nanotechnology. pp. 312-320; Jul. 8, 2010).*

Frey et al. "Electrospinning and Porosity Measurements of Nylon6 PEO blended Nonwovens" Journal of Engineered Fibers and Fabrics (2007), 2(1):31-37.

Hashi et al. "Antithrombogenic Modification of Small Diameter Microfibrous Vascular Grafts" Arterioscler Thromb Vasc Biol. (Aug. 2010), 30(8):1621-1627.

(Continued)

*Primary Examiner* — Anna Falkowitz
(74) *Attorney, Agent, or Firm* — Pepper Hamilton LLP

(57) ABSTRACT

A synthetic construct suitable for implantation into a biological organism that includes at least one polymer scaffold; wherein the at least one polymer scaffold includes at least one layer of polymer fibers that have been deposited by electrospinning; wherein the orientation of the fibers in the at least one polymer scaffold relative to one another is generally parallel, random, or both; and wherein the at least one polymer scaffold has been adapted to function as at least one of a substantially two-dimensional implantable structure and a substantially three-dimensional implantable tubular structure.

11 Claims, 5 Drawing Sheets

(56) References Cited

U.S. PATENT DOCUMENTS

| | | |
|---|---|---|
| 2007/0142907 A1 | 6/2007 | Moaddeb et al. |
| 2007/0191956 A1 | 8/2007 | Prewett et al. |
| 2007/0269481 A1 | 11/2007 | Li et al. |
| 2007/0286880 A1 | 12/2007 | Vasiliev et al. |
| 2008/0208358 A1 | 8/2008 | Bellamkonda et al. |
| 2009/0018643 A1 | 1/2009 | Hashi et al. |
| 2009/0108503 A1 | 4/2009 | Scott-Carnell et al. |
| 2009/0143855 A1 | 6/2009 | Weber et al. |
| 2010/0082114 A1 | 4/2010 | Gingras et al. |
| 2010/0105799 A1 | 4/2010 | Rudd et al. |
| 2010/0166854 A1 | 7/2010 | Michniak-Kohn et al. |
| 2010/0222771 A1 | 9/2010 | Mitchell et al. |
| 2010/0233115 A1 | 9/2010 | Patel et al. |
| 2010/0273258 A1 | 10/2010 | Lannutti et al. |
| 2010/0303881 A1 | 12/2010 | Hoke et al. |
| 2011/0022149 A1 | 1/2011 | Cox et al. |
| 2011/0028834 A1 | 2/2011 | Zussman |
| 2011/0030885 A1* | 2/2011 | Anneaux .......... A61L 31/06 156/187 |
| 2011/0070283 A1 | 3/2011 | Hossainy et al. |
| 2011/0083987 A1 | 4/2011 | Rolland et al. |
| 2011/0098826 A1 | 4/2011 | Mauck et al. |
| 2011/0166647 A1 | 7/2011 | Hashi et al. |
| 2011/0177395 A1 | 7/2011 | Kamisasa |
| 2011/0270412 A1 | 11/2011 | Bellan et al. |
| 2012/0068384 A1 | 3/2012 | Phaneuf et al. |
| 2012/0093717 A1 | 4/2012 | Mauck et al. |
| 2012/0271405 A1 | 10/2012 | Soletti |
| 2013/0103079 A1 | 4/2013 | Lau et al. |
| 2013/0150963 A1 | 6/2013 | Johnson |
| 2013/0310920 A1 | 11/2013 | Su |
| 2014/0030315 A1 | 1/2014 | Johnson |
| 2014/0057346 A1 | 2/2014 | Johnson |
| 2014/0072951 A1 | 3/2014 | Johnson |
| 2014/0271795 A1 | 9/2014 | Phaneuf et al. |
| 2014/0272225 A1 | 9/2014 | Johnson |
| 2014/0309726 A1* | 10/2014 | Wang .......... A61L 27/56 623/1.46 |

FOREIGN PATENT DOCUMENTS

| | | |
|---|---|---|
| EP | 2422003 | 10/2010 |
| JP | 2012-527217 A | 11/2012 |
| WO | WO 00/10622 A1 | 3/2000 |
| WO | WO 01/15754 A1 | 3/2001 |
| WO | WO 2005/012606 A2 | 2/2005 |
| WO | WO 2005/096989 A1 | 10/2005 |
| WO | WO 2006/138552 A2 | 12/2006 |
| WO | WO 2008/137659 A1 | 11/2008 |
| WO | WO 2009/089035 A1 | 7/2009 |
| WO | WO 2010/040129 A3 | 4/2010 |
| WO | WO 2010/048281 A1 | 4/2010 |
| WO | WO 2010/124207 A1 | 10/2010 |
| WO | WO 2013/078051 A1 | 5/2013 |
| WO | WO 2013/106822 A1 | 7/2013 |
| WO | WO 2014/031721 A1 | 2/2014 |
| WO | WO 2014/145864 A1 | 9/2014 |
| WO | WO 2015/153011 A1 | 10/2015 |

OTHER PUBLICATIONS

Aboitiz et al. "Fiber composition of the human corpus callosum" (Dec. 11, 1992) Brain Res. 598(1-2):143-153 (Abstract only).
Albertini et al. "The effect of glycosaminoglycans and proteoglycans on lipid peroxidation" (Aug. 2000) Int. J. Mol. Med. 6(2):129-136 (Abstract only).
Alexis et al. "In Vivo Particle Uptake by Airway Macrophages in Healthy Volunteers" (2006) Am. J. Respir. Cell Mol. Biol. 34(3):305-313.
Band et al. "Antiproliferative effect of gossypol and its optical isomers on human reproductive cancer cell lines" (Mar. 1989) Gynecologic Oncology 32(3):273-277 (Abstract only).
Bandtlow et al. "Proteoglycans in the developing brain: new conceptual insights for old proteins" (Oct. 2000) Physiol. Rev. 80(4):1267-1290.
Baran et al. "Important roles for macrophage colony-stimulating factor, CC chemokine ligand 2, and mononuclear phagocytes in the pathogenesis of pulmonary fibrosis" (2007) Am. J. Respir. Crit. Care Med. 176(1):78-89.
Bellail et al. "Microregional extracellular matrix heterogeneity in brain modulates glioma cell invasion" (Jun. 2004) Int. J. Biochem. Cell Biol. 36(6):1046-1069 (Abstract only).
Beningo et al. "Nascent Focal Adhesions Are Responsible for the Generation of Strong Propulsive Forces in Migrating Fibroblasts" (May 14, 2001) J. Cell Biol. 153(4):881-887.
Benz et al. "Biochemical Correlates of the Antitumor and Antimitochondrial Properties of Gossypol Enantiomers" (Jun. 1990) Mol. Pharma. 37(6):840-847 (Abstract only).
Benz et al. "Lactic Dehydrogenase Isozymes, $^{31}$P Magnetic-Resonance Spectroscopy, and In Vitro Antimitochondrial Tumor Toxicity With Gossypol and Rhodamine-123" (Feb. 1987) J. Clin. Invest. 79(2):517-523.
Benz et al. "Selective toxicity of gossypol against epithelial tumors and its detection by magnetic resonance spectroscopy" (Mar. 1988) Contraception 37(3):221-228 (Abstract only).
Bernstein et al. "Glioblastoma cells do not intravasate into blood vessels" (Jan. 1995) Neurosurgery 36(1):124-132 (Abstract only).
Bershadsky et al. "Adhesion-mediated mechanosensitivity: a time to experiment, and a time to theorize" (Oct. 2006) Curr. Opn. Cell Biol. 18(5):472-481 (Abstract only).
Binder et al. "Proteases and the Biology of Glioma Invasion" (2002) J. Neuro-Oncology 56:149-158.
Bucala et al. "Circulating Fibrocytes Define a New Leukocyte Subpopulation That Mediates Tissue Repair" (Nov. 1994) Mol. Med. 1(1):71-81 (Abstract only).
Camoretti-Mercado "Targeting the airway smooth muscle for asthma treatment" (Oct. 2009) Translational Research 154(4):165-174 (Abstract only).
Cattaruzza et al. "Proteoglycan control of cell movement during wound healing and cancer spreading" (Sep. 2005) Matrix Biol. 24(6):400-417 (Abstract only).
Central Brain Tumor Registry of the United States, Primary Brain Tumors in the United States—Statistical Report 1998-2002, CBTRUS 2005-2006.
Chalmers et al. "Chapter 9. Preparative applications of magnetic separation in biology and medicine" (2007) Laboratory Techniques in Biochemistry and Molecular Biology 32:249-264 (Abstract only).
Chen et al., Preparation and Characterization of Coaxial Electrospun Thermoplastic Polyurethane/Collagen Compound Nanofibers for Tissue Engineering Applications, Colloids and Surfaces B-Biointerfaces (2010), 79(2):315-325.
Chew et al. "The Role of Electrospinning in the Emerging Field of Nanomedicine" 2006, Curr. Pharm. Sec. 12(36)A:4751-4770.
Chicoine et al. "Assessment of brain-tumor cell motility in vivo and in vitro" (Apr. 1995) J. Neurosurg. 82(4):615-622 (Abstract only).
Choi et al. "Structuring electrospun polycaprolactone nanofiber tissue scaffolds by femtosecond laser ablation" (Nov. 2007) J. Laser Appl. 19(4):225-231.
Cukierman et al. "Taking cell-matrix adhesions to the third dimension" (Nov. 23, 2001) Science 294:1708-1712.
Dahl et al., "Readily Available Tissue-Engineered Vascular Grafts" (2011) Science Translational Medicine, 3(68).
Davies et al. "Adult axon regeneration in adult CNS white matter" (Dec. 1, 1998) Trends Neurosci. 21(12):515.
Delpech et al. "Hyaluronan and hyaluronectin in the nervous system" (Sep. 28, 2007) Ciba Foundation Symposium 143—The Biology of Hyaluronan (Abstract only).
Diaz et al. "Controlled encapsulation of hydrophobic liquids in hydrophilic polymer nanofibers by co-electrospinning" (2006) Adv. Funct. Mater. 16(16):2110-2116.
Discher et al. "Tissue cells feel and respond to the stiffness of their substrate" (Nov. 18, 2005) Science 310:1139-1143.
Drilling et al. "Fabrication of burst pressure competent vascular grafts via electrospinning: Effects of microstructure" (Mar. 15, 2009) J. Miomed. Mat. Res. Part A 88A(4):923-934 (Abstract only).

(56) References Cited

OTHER PUBLICATIONS

Duling et al. "Mechanical characterization of electrospun Polycaprolactone (PCL): a potential scaffold for tissue engineering" (Feb. 2008) *J. Biomech. Eng.* 130(1) No. 011006 (Abstract only).
Engler et al. "Matrix Elasticity Directs Stem Cell Lineage Specification" (Aug. 25, 2006) *Cell* 126(4):677-689.
Epperly et al. "Correlation of Ionizing Irradiation-induced Late Pulmonary Fibrosis with Long-term Bone Marrow Culture Fibroblast Progenitor Cell Biology in Mice Homozygous Deletion Recombinant Negative for Endothelial Cell Adhesion Molecules" (2004) *In Vivo* 18(1):1-14.
Farin et al. "Transplanted glioma cells migrate and proliferate on host brain vasculature: a dynamic analysis" (Jun. 2006) *Glia* 53(8):799-808 (Abstract only).
Fathallah-Shaykh "Darts in the Dark Cure Animal, but Not Human, Brain Tumors" (May 2002) *Arch. Neural.* 59:721-724 (Abstract only).
Fujihara et al "Guided bone regeneration membrane made of Polycaprolactone/calcium carbonate composite nano-fibers" (Jul. 2005) *Biomaterials* 26(19):4139-4147 (Abstract only).
Furnari et al. "Malignant astrocytic glioma: genetics, biology, and paths to treatment" (2007) *Genes Dev.* 21:2683-2710.
Gaumer et al. "Structure-function relationships and Source-to-ground Distance and the Mechanical Properties of Electrospun Fiber" *Acta Biomaterialia* 5(5):1552-1561 (Abstract only).
Geiser et al. "The Role of Macrophages in the Clearance of Inhaled Ultrafine Titanium Dioxide Particles" (2008) *Am. J. Respir. Cell Mol. Biol.* 38(3):371-376.
Georges et al. "Cell type-specific response to growth on soft materials" (Apr. 2005) *J. Appl. Physiol.* 98:1547-1553.
Georges et al. "Matrices with compliance comparable to that of brain tissue select neuronal over glial growth in mixed cortical cultures" (Apr. 2006) *Biophys. J.* 90:3012-3018.
Giese et al. "Dichotomy of astrocytoma migration and proliferation" (1996) *Int. J. Cancer* 67:275-282.
Giese et al. "Glioma cell adhesion and migration on human brain sections" (1998) *Anticancer Res.* 18(4A):2435-2447 (Abstract only).
Giese et al. "Migration of Human Glioma Cells on Myelin" (Apr. 1996) *Neurosurgery* 38(4):755-764 (Abstract only).
Giese et al. "Substrates for astrocytoma invasion" (Aug. 1995) *Neurosurgery* 37(2):294-302 (Abstract only).
Gilbert et al. "Antiproliferative activity of gossypol and gossypolone on human breast cancer cells" (May 26, 1995) *Life Sciences* 57(1):61-67 (Abstract only).
Gladson "The Extracellular Matrix of Gliomas: Modulation of Cell Function" (Oct. 1999) *J. Neuropath. Exper. Neur.* 58(10):1029-1040 (Abstract only).
Goldbrunner et al. "Cell-extracellular matrix interaction in glioma invasion" (1999) *Acta Neurochir (Wien)* 141:295-305.
Grandpre et al. "Nogo: a molecular determinant of axonal growth and regeneration" (Oct. 2001) *Neuroscientist* 7(5):377-386 (Abstract only).
Haley et al. "Study of myelin purity in relation to axonal contamination" (1980) *Cell Mol. Neurobiol.* 1:175-187.
Hashi et al. "Antithrombogenic Property of Bone Marrow Mesenchymal Stem Cells in Nanofibrous Vascular Grafts" Jul. 17, 2007, *PNAS* 104(29) pp. 11915-11920.
He et al. "Fabrication of Drug-Loaded Electrospun Aligned Fibrous Threads for Suture Applications" 2009, J. Biomed. Mater. Research, Part A 89(1):80-95.
Hinz et al. "Alpha-smooth muscle actin expression upregulates fibroblast contractile activity" (Sep. 2001) *Molecular Biology of the Cell* 12(9):2730-2741.
Holland "Glioblastoma multiforme; the terminator" (Jun. 6, 2000) *PNAS USA* 97(12):6242-6244.
Hsu et al. "N,N-Dimethylformamide Additions to the Solution for the Electrospinning of Poly(ε-caprolactone) Nanofibers" (Apr. 2004) *Macromolecular Materials and Engineering* 289(4):334-340.

Hsu et al. "Nano-sized beads and porous fiber constructs of Poly(ε-caprolactone) produced by electrospinning" (2004) *Journal of Material Science* 39(9):3003-3013.
Hu et al. "Gossypol inhibits basal and estrogen-stimulated DNA synthesis in human breast carcinoma cells" (1993) *Life Sciences* 53(25):PL433-PL438 (Abstract only).
Hu et al. "Regulating axon growth within the postnatal central nervous system" (Dec. 2004) *Semin Perinatol* 28(6):371-378.
Hu et al. "The proteoglycan brevican binds to fibronectin after proteolytic cleavage and promotes glioma cell motility"(Sep. 5, 2008) *Journal of Biological Chemistry* 283(36):24848-24859.
Huang et al. "A review on polymer nanofibers by electrospinning and their applications in nanocomposites" (Nov. 2003) *Composites Science and Technology* 63(15):2223-2253 (Abstract only).
International Search Report and Written Opinion for PCT/US2015/016973 dated May 22, 2015.
Jaroszewski et al. "Action of Gossypol and Rhodamine 123 on Wild Type and Multidrug-resistant MCF-7 Human Breast Cancer Cells: $^{31}$P Nuclear Magnetic Resonance and Toxicity Studies" (1990) *Cancer Research* 50(21):6936-6943.
Johnson "First-in-the-World Equine Joint Injection for Osteoarthritis" (Jul./Aug. 2014) *The International Equine Veterinarian* 23-25.
Johnson et al. "Electrospun PCL in Vitro: a Microstructural Basis for Mechanical Property Changes" (2009) *Journal of Biomaterials Science, Polymer Edition* 20(4):467-481 (Abstract only).
Johnson et al. "Microstructure-Property Relationships in a Tissue-Engineering Scaffold" (2007) *Journal of Applied Polymer Science* 104(5):2919-2927.
Johnson et al. "Quantitative Analysis of Complex Glioma Cell Migration on Electrospun Polycaprolcatone Using Time-Lapse Microscopy" (2009) *Tissue Engineering Part C* 15(4):531-540.
Jung et al. "Tracking the invasiveness of human astrocytoma cells by using green fluorescent protein in an organotypical brain slice model" (Jan. 2001) *J. Neurosurgery* 94(1):80-89 (Abstract only).
Kang et al. Plasma Treatment of Textiles—synthetic Polymer-Base Textiles (2004) *AATCC Review* 4(11):29-33.
Katta et al. "Continuous electrospinning of aligned polymer nanofibers onto a wire drum collector" (Sep. 28, 2004) *Nano Letters* 4(11):2215-2218 (Abstract only).
Kazemnejad et al. "Biochemical and Molecular Characterization of Hepatocyte-Like Cells Derived from Human Bone Marrow Mesenchymal Stem Cells on a Novel Three-Dimensional Biocompatible Nanofibrous Scaffold" Feb. 1, 2009, *J. Gastronenter. Hepatol.* 24(2):278-287.
Khil et al. "Novel fabricated matrix via electrospinning for tissue engineering" (2005) *Journal of Biomedical Materials Research Part B—Applied Biomaterials* 72B(1):117-124.
Kim et al. "Controlled protein release from electrospun biodegradable fiber mesh composed of poly(ε-caprolactone) and poly(ethylene oxide)" (Jun. 29, 2007) *International Journal of Pharmaceutics* 338 (1-2):276-283 (Abstract only).
Kim et al. "Epithelial cell α3β1 integrin links β-catenin and Smad signaling to promote myofibroblast formation and pulmonary fibrosis" (Jan. 2009) *Journal of Clinical Investigation* 119(1):213-224.
Kleihues et al. "The WHO Classification of Tumors of the Nervous System" (Mar. 2002) *J. Neuropathol. Exp. Neurol.* 61(3):215-225 (Abstract only).
Klim et al. "A Defined Glycosaminoglycan-Binding Substratum for Human Pluripotent Stem Cells" (2010) *Nature Methods* 7(23):989-996 (Abstract only).
Ko et al. "High Percentage of False-Positive Results of Cytokeratin 19 RT-PCR in Blood: A Model for the Analysis of Illegitimate Gene Expression" (2000) *Oncology* 59:81-88 (Abstract only).
Kwon et al. "Electrospun nano- to microfiber fabrics made of biodegradable copolyesters: structural characteristics, mechanical properties and cell adhesion potential" (Jun. 2005) *Biomaterials* 26(18):3929-3939.
Lannutti et al. "Electrospinning for tissue engineering scaffolds" (Apr. 2007) *Materials Science and Engineering: C* 27(3):504-509.
Leblanc et al. "An in vitro study of inhibitory activity of gossypol, a cottonseed extract, in human carcinoma cell lines" (Dec. 2002) *Pharmacological Research* 46(6):551-555.

(56) References Cited

OTHER PUBLICATIONS

Lee et al. "Characterization of nano-structured poly(ε-caprolactone) nonwoven mats via electrospinning" (Feb. 2003) *Polymer* 44(4):1287-1294.

Lesma et al. "Glycosaminoglycans in nerve injury: I. Low doses glycosaminoglycans promote neurite formation" (Dec. 1, 1996) *J. Neurosci. Res.* 46(5):565-571.

Levicar et al. "Proteases in brain tumour progression" (2003) *Acta Neurochir. (Wien.)* 145:825-838.

Levina et al. "Chemotherapeutic drugs and human tumor cells cytokine network" (2008) *International Journal of Cancer* 123(9):2031-2040.

Li et al. "A three-dimensional nanofibrous scaffold for cartilage tissue engineering using human mesenchymal stem cells" (Feb. 2005) *Biomaterials* 26(6):599-609.

Li et al. "Biological response of chondrocytes cultured in three-dimensional nanofibrous poly(ε-caprolactone) scaffolds" (Dec. 15, 2003) *Journal of Biomedical Materials Research Part A* 67A(4):1105-1114.

Li et al. "Electrospinning nanofibers as uniaxially aligned arrays and layer-by-layer stacked films" (Feb. 2004) *Advanced Materials* 16(4):361-366.

Li et al. "Multilineage differentiation of human mesenchymal stem cells in a three-dimensional nanofibrous scaffold" (Sep. 2005) *Biomaterials* 26(25):5158-5166.

Liang et al. "Developing gossypol derivatives with enhanced anti-tumor activity" (1995) *Investigational New Drugs* 13(3):181-186.

Lieblein et al. "STAT3 can be activated through paracrine signaling in breast epithelial cells" (2008) *BMC Cancer* 8(302):1-14 :302.

Liu et al. "Function analysis of estrogenically regulated protein tyrosine phosphatase γ (PTPγ) in human breast cancer cell line MCF-7" (2004) *Oncogene* 23(6):1256-1262.

Liu et al. "Involvement of breast epithelial-stromal interactions in the regulation of protein tyrosine phosphatase-γ (PTPγ) mRNA expression by estrogenically active agents" (2002) *Breast Cancer Research and Treatment* 71(1):21-35.

Liu et al. The (−)-enantiomer of gossypol possesses higher anticancer potency than racemic gossypol in human breast cancer: (2002) *Anticancer Research* 22(1A):33-38.

Liu et al. "Transformation of MCF-10A Human Breast Epithelial Cells by Zeranol and Estradiol-17beta" (Nov.-Dec. 2004) *Breast J.* 10(6):514-521 (Abstract only).

Lo et al. "Cell movement is guided by the rigidity of the substrate" (Jul. 2000) *Biophysical Journal* 79(1);144-152.

Luu et al. "Development of a nanostructured DNA delivery scaffold via electrospinning of PLGA and PLGA and PLA-PEG block copolymers" (Apr. 29, 2003) *Journal of Controlled Release* 89(2):341-353.

Macchiarini et al. "Clinical Transplantation of a Tissue-Engineered Airway" (Dec. 13, 2008) *The Lancet* 372(9655):2023-2030.

Martins et al. "Electrospun nanostructured scaffolds for tissue engineering applications" (2007) *Nanomedical* 2(6):929-942.

Mathews, "Preparation and anisotropic mechanical behavior of highly-oriented electrospun poly(butylene terephthalate) fibers" (Aug. 2006) *Journal of Applied Polymer Science* 101(3):2017-2021.

McClure et al. "A Three-Layered Electrospun Matrix to Mimic Native Arterial Architecture Using Polycaprolactone, Elastin, and Collagen: A Preliminary Study" 2010, *Acta Biomaterialia* 6:2422-2433.

Morawski et al. "Perineuronal nets potentially protect against oxidative stress" (Aug. 2004) *Exp. Neurol.* 188(2):309-315.

Morgenstern et al. "Chondroitin sulphate proteoglycans in the CNS injury response" (2002) *Prog. Brain Res.* 137:313-332.

Mori et al. "Fibrocytes contribute to the myofibroblast population in wounded skin and originate from the bone marrow" (Mar. 10, 2005) *Experimental Cell Research* 304(1):81-90.

Murray et al. "Hyper-responsiveness of IPF/UIP fibroblasts: Interplay between TGF β1, IL-13 and CCL2" (2008) 40(10):2174-2182.

Nam et al. "Improved Cellular Infiltration in Electrospun Fiber via Engineered Porosity" (Sep. 2007) *Tissue Engineering* 13(9):2249-2257.

Nam et al. "Materials selection and residual solvent retention in biodegradable electrospun fibers" (Feb. 5, 2008) *Journal of Applied Polymer Science* 107(3):1547-1524.

Nam et al. "Modulation of Embryonic Mesenchymal Progenitor Cell Differentiation via Control Over Pure Mechanical Modulus in Electrospun Nanofibers" (Apr. 2011) *Acta Biomaterialia* 7(4):1516-1524.

Nam et al. "Novel Electrospun Scaffolds for the Molecular Analysis of Chondrocytes Under Dynamic Compression" 2009, *Tissue Engineering Part A* 15(3):513-523.

Ninomiya et al. "Transforming Growth Factor—βSignaling Enhances Transdifferentiation of Macrophages into Smooth Muscle-Like Cells" (2006) *Hypertension Research* 29(4):269-276.

Norton et al. "Myelination in rat brain: method of myelin isolation" (Oct. 1973) *J. Neurochem.* 21(4):749-757.

Novak et al. "Extracellular matrix and the brain: components and function" (2000) *J. Clin. Neurosci.* 7(4):280-290.

Ohnishi et al. "A Novel Model of Glioma Cell Invasion Using Organotypic Brain Slice Culture" (Jul. 15, 1998) *Cancer Res.* 58:2935-2940.

Palfi et al. "Correlation of in vitro infiltration with glioma histological type in organotypic brain slices" (2004) *Br. J. Cancer* 91(4):745-752.

Pelham Jr. et al. "Cell locomotion and focal adhesions are regulated by substrate flexibility" (Dec. 1997) *PNAS USA* 94:13661-13665.

Pham et al., Electrospinning of Polymeric Nanofibers for Tissue Engineering Applications: A Review, Tissue Engineering (2006), 12(5):1197-1211.

Pilkington "The paradox of neoplastic glial cell invasion of the brain and apparent metastatic failure" (1997) *Anticancer Res.* 17(6B):4103-4105 (Abstract).

Powell et al. "EDC cross-linking improves skin substitute strength and stability" (2006) *Biomaterials* 27(34): 5821-5827.

Properzi et al. "Proteoglycans and Brain Repair" (Feb. 2004) *News Physiol. Sci.* 19:33-38.

Quigley et al. "The relationship between survival and the extent of the resection in patients with supratentorial malignant gliomas" (1991) *Neurosurgery* 29:385-389.

Rao "Molecular mechanisms of glioma invasiveness: the role of proteases" (Jul. 2003) *Nature Reviews Cancer* 3:489-501.

Rath et al. "Compressive Forces Induce Osteogenic Gene Expression in Calvarial Osteoblasts" (2008) *Journal of Biomechanics* 41(5):1095-1103.

Rauch "Extracellular matrix components associated with remodeling processes in brain" (2004) *Cell Mol. Life Sci.* 61:203102045.

Reneker et al. "Nanometre diameter fibres of polymer, produced by electrospinning" (1996) *Nanotechnology* 7(3):216-223.

Rocks et al. "ADAMTS-1 Metalloproteinase Promotes Tumor Development through the Induction of a Stromal Reaction In vivo" (2008) *Cancer Research* 68(22):9541-9550.

Ruoslahti "Brain extracellular matrix" (1996) *Glycobiologhy* 6(5):489-492.

Sasmono et al. "A macrophage colony-stimulating factor receptor—green fluorescent protein transgene is expressed throughout the mononuclear phagocyte system of the mouse" (2003) *Blood* 101(3):1155-1163.

Saunders et al. "Fibrocyte localization to the airway smooth muscle is a feature of asthma" (Feb. 2009) *Journal of Allergy and Clinical Immunology* 123(2): 376-384.

Schiffer et al. "Cell proliferation and invasion in malignant gliomas" (1997) *Anticancer Research* 17(1A):61-69 (Abstract only).

Schmidt et al. "Identification of Circulating Fibrocytes as Precursors of Bronchial Myofibroblasts in Asthma" (2003) *Journal of Immunology* 171(1):380-389.

Shin et al. "Contractile cardiac grafts using a novel nanofibrous mesh" (Aug. 2004) *Biomaterials* 25(17):3717-3723.

Shin et al. "In Vivo Bone Tissue Engineering Using Mesenchymal Stem Cells on a Novel Electrospun Nanofibrous Scaffold" (Jul. 9, 2004) *Tissue Engineering* 10(1-2):33-41.

(56) References Cited

OTHER PUBLICATIONS

Sieben et al. "PCR artifacts in LOH and MSI analysis of microdissected tumor cells" (Nov. 2000) *Human Pathology* 31(11):1414-1419.
Silver et al. "Regeneration beyond the glial scar" (Feb. 2004) *Nature* 5:146-156.
Srikar et al. "Desorption-limited mechanism of release from polymer nanofibers" (2008) *Langmuir* 24(3):965-974.
Stein et al. "Estimating the cell density and invasive radius of three-dimensional glioblastoma tumor spheroids grown in vitro" (Aug. 1, 2007) *Applied Optics* 46(22):5110-5118.
Stitzel et al. "Controlled Fabrication of a Biological Vascular Substitute" 2006, *Biomaterials* 27:1088-1094.
Subramanian et al. "Metastasis to and from the central nervous system—the 'relatively protected site'" (Aug. 2002) *The Lancet Oncology* 3(8):498-507.
Swanson et al. "A quantitative model for differential motility of gliomas in grey and white matter" (Oct. 2000) *Cell Proliferation* 33(5):317-329.
Swanson "Quantifying glioma cell growth and invasion in vitro" (2008) *Mathematical and Computer Modeling* 47:638-648.
Teo et al. "A review on electrospinning design and nanofibre assemblies" (2006) *Nanotechnology* 17(14):R89-R106.
Teo et al. "Electrospun fibre bundle made of aligned nanofibers over two fixed points" (1978) *Nanotechnology* 16:1878-1884.
Thomas et al. "Effects of gossypol on the cell cycle phases in T-47D human breast cancer cells" (Jul.-Aug. 1991) *Anticancer Research* 11(4):1469-1476 (Abstract only).
Tomlinson et al. "Loss of heterozygosity analysis: Practically and conceptually flawed?" (2002) *Genes Chromosomes & Cancer* 34:349-353.
Tonn et al. "Mechanisms of glioma cell invasion" (2003) *Acta Neurochir* Suppl 88: 163-167.
Toole "Hyaluronan and its binding proteins, the hyaladherins" (1990) *Curr. Opin. Cell Biol.* 2:839-844.
Tse, et al. "Current Status of Pipeline Embolization Device in the Treatment of Intracranial Aneurysms: A review" (Dec. 2013) *World Neurosurgery* 80(6): 829-835.
Tuszynski et al. "Differential cytotoxic effect of gossypol on human melanoma, colon carcinoma, and other tissue culture cell lines" (Feb. 1984) *Cancer Research* 44(2):768-771.
Van Meter et al. "The role of matrix metalloproteinase genes in glioma invasion: co-dependent and interactive proteolysis" (2001) *Journal of Neuro-Oncology* 53:213-235.
Viapiano et al. "BEHAB/brevican requires ADAMTS-mediated proteolytic cleavage to promote glioma invasion" (2008) *J. Neurooncol.* 88:261-272.
Viapiano et al. "From barriers to bridges: chondroitin sulfate proteoglycans in neuropathology" (Oct. 2006) *Trends Mol. Med.* 12(10):488-496.
Vuorinen et al. "Debulking or biopsy of malignant glioma in elderly people—10andomized study" (2003) *Acta Neurochir.* 145:5-10.
Wang et al. "Conjugated Linoleic Acid (CLA) Up-regulates the Estrogen-regulated Cancer Suppressor Gene, Protein Tyrosine Phosphatase ϵ (PTPϵ), in Human Breast Cells" (2006) *Anticancer Research* 26(1A):27-34.
Wang et al. "Effect of gossypol on DNA synthesis and cell cycle progression of mammalian cells in vitro" (Jan. 1984) *Cancer Research* 44(1):35-38.
Wang et al. "Nanofibres and their Influence on Cells for Tissue Regeneration" (2005) *Aust. J. Chem.* 58(10):704-712.
Wang et al. "Increased Circulating Fibrocytes in Asthma with Chronic Airflow Obstruction" (2008) *Am. J. Respir. Crit. Care Med.* 178(6): p. 583-591.
Williams et al. "Anti-glioma effects of protein kinase inhibitors that simultaneously block invasion and proliferation" (Oct. 2007) Abstracts from 12$^{th}$ Annual Meeting of the Society for Neuro-Oncology 9: 486 ET-18 (Abstract only).
Wu et al. "Versican protects cells from oxidative stress-induced apoptosis" (Feb. 2005) *Matrix Biology* 24(1):3-13.
Wu et al. "An in vitro and in vivo study of antitumor effects of gossypol on human SW-13 adrenocortical carcinoma" (1986) *Cancer Research* 49(14):3754-3758.
Wykosky et al. "Soluble monomeric EphrinA1 is released from tumor cells and is a functional ligand for the EphA2 receptor" (2008) *Oncogene* 27(58):7260-7273.
Xie et al. "Encapsulation of protein drugs in biodegradable microparticles by co-axial electrospray" Jan. 15, 2008) *Journal of Colloid and Interface Science* 317(2):469-476.
Xie et al. "White matter inhibitors in CNS axon regeneration failure" (Feb. 2007) *Exp. Neurol.* 209(2):302-312.
Yamaguchi "Lecticans: organizers of the brain extracellular matrix" (2000) *Cell Mol. Life Sci.* 57:276-289.
Yang et al. "Integrin α1β1 and α2β1are the key regulators of hepatocarcinoma cell invasion across the fibrotic matrix microenvironment" (Dec. 1, 2003) *Cancer Research* 63(23): 8312-8317.
Yoo et al. "Surface-Functionalized Electrospun Nanofibers for Tissue Engineering and Drug Delivery" Jan. 1, 2009, *Advanced Drug Delivery Reviews* 61:1033-1042.
Yoshimoto et al. "A biodegradable nanofiber scaffold by electrospinning and its potential for bone tissue engineering" (May 2003) *Biomaterials* 24(12):2077-2082.
Yu et al. "Production of submicrometer diameter fibers by two-fluid electrospinning" (Sep. 2004) *Adv. Mater.* 16(17):1562-1566.
Zborowski et al. "Red blood cell magnetophoresis" (Apr. 2003) *Biophysical Journal* 84:2638-2645.
Zeng et al. "Enzymatic degradation of poly(L-lactide) and poly(α-caprolactone) electrospun fibers" (Dec. 15, 2004) *Macromolecular Bioscience* 4(12):1118-1125.
Zeng et al. "Ultrafine fibers electrospun from biodegradable polymers" (Jul. 25, 2003) *Journal of Applied Polymer Science* 89(4):1085-1092.
Zhang et al. "Electrospinning of gelatin fibers and gelatin/PCL composite fibrous scaffolds" (2005) *J. Biomed. Mater. Res. Part B: Appl. Biomater.* 72B(1):156-165.
Zhang et al. "Recent development of polymer nanofibers for biomedical and biotechnological applications" (2005) *Journal of Materials Science—Materials in Medicine* 16(10):933-946.
International Search Report and Written Opinion for PCT/US2016/030058 dated Jul. 29, 2016.
Samios et al., "In situ Compatibilization of polyurethane with poly(ethylene terephthalate)," Department of Chemistry, European Polymer Journal (2000), 36 pp. 937-947.
International Search Report and Written Opinion for International Application No. PCT/US2016/060157 dated Jan. 31, 2017.
Lee et al., "Biomedical Applications of Magnetically Functionalized Organic/Inorganic Hybrid Nanofibers," International Journal of Molecular Sciences (Jun. 15, 2015), 16 pp. 13661-13677.

\* cited by examiner

FIBER SCAFFOLDS FOR USE CREATING IMPLANTABLE STRUCTURES

CROSS-REFERENCE TO RELATED APPLICATIONS

This patent application claims the benefit of U.S. Provisional Patent Application Ser. No. 61/882,504 filed on Sep. 25, 2013, and entitled "Fiber Scaffolds for Use in Arteriovenus Shunts and Vascular Grafts", the disclosure of which is hereby incorporated by reference herein in its entirety and made part of the present U.S. utility patent application for all purposes.

BACKGROUND OF THE INVENTION

Tissue engineering typically involves the synthesis of biologically relevant tissue for a wide range of applications including the replacement or support of damaged organs. A common strategy is culturing target specific cells in vitro in a scaffold followed by implantation of the scaffold into a biological organism. As a logical cellular source for tissue engineering, stem cells have attracted a great deal of attention due to their relatively fast rate of proliferation and diverse differentiation potential for various phenotypes. These include cells derived from several origins: induced pluripotent stem cells from fibroblasts, mesenchymal stem cells from bone marrow and adult stem cells from adipose tissue. Stem cells self-renew and their terminal differentiation depends on the influence of certain soluble molecules (e.g., growth factors, cytokines, etc.) as well as physical and biochemical interactions with the scaffold. Cellular behavior and subsequent tissue development at the cell-scaffold interface, therefore, involve adhesion, motility, proliferation, differentiation and functional maturity. The physicochemical properties of a scaffold, such as bulk chemistry, surface chemistry, topography, three-dimensionality and mechanical properties, all influence cellular response. Bulk chemistry can control cytotoxicity, as most scaffolds are made of biodegradable materials and must eventually release the by-products of their degradation. The effect of surface chemistry is often mediated by instantly adsorbed proteins such as fibronectin, collagen, fibrinogen, vitronectin, and immunoglobulin that affect phenotype, viability, and morphology, as well as proliferation and differentiation.

Studies regarding the effect of surface topography and texture on cellular response have been conducted. Stem cells are known to recognize topographical features on the order of hundreds of nanometers to several micrometers and exhibit distinctive genomic profiles in the absence of biochemical differentiation cues as well as a commitment to terminal differentiation. Electrospun scaffolds are ideal matrices for three-dimensional (3D) culture of cells and provide non-woven nano- to micro-sized fibrous microstructures typically having relative porosities of 70-90%. Natural biodegradable materials such as collagen, gelatin, elastin, chitosan, and hyaluronic acid, as well as synthetic biodegradable polymers such as poly(e-caprolactone) (PCL), poly(glycolic) acid (PGA) and poly(lactic) acid (PLA), have been electrospun for chondral and osseous applications.

In general, the broad utility of electrospun scaffolds for tissue engineering, wound healing, and organ replacement is clear (see *Modulation of Embryonic Mesenchymal Progenitor Cell Differentiation via Control Over Pure Mechanical Modulus in Electrospun Nanofibers*, Nama et al., Acta Biomaterialia 7, 1516-1524 (2011), which is incorporated by reference herein in its entirety, for all purposes) and the present invention provides, more specifically, polymer fiber constructs for use in the creation of nanofiber patches, as well as conduits for use in arteriovenous shunts for hemodialysis and blood vessel graft applications.

With regard to the creation of arteriovenous shunt grafts, the dysfunction of arteriovenous shunts in hemodialysis patients represents the single most common and burdensome complication in patients with end stage renal disease (see, *US Renal Data System*. USRDS Annual data report (2002); and *Vascular Access in Hemodialysis: Issues, Management, and Emerging Concepts*, Roy-Chaudhary et al., Cardiol Clin 23, 249-273 (2005), which are incorporated by reference herein in their entirety, for all purposes). More than 20% of all Medicare patients with end stage renal disease (ESRD) have vascular access graft complications that cost the U.S. healthcare system billions of dollars per year in access site treatment costs (see, *Hemodialysis vascular access morbidity*, Feldman HI, Kobrin S, Wasserstein A, *J Am Soc Nephrol* 7, 523-35 (1996) and *Vascular Access in Hemodialysis: Issues, Management, and Emerging Concepts*, Roy-Chaudhary et al., Cardiol Clin 23, 249-273 (2005), which are incorporated by reference herein in their entirety, for all purposes. In most of these patients, there are basically two approaches to establishing a vascular access site. The first approach is to create a native arteriovenous fistula by surgically anastomosing a larger artery to a vein, with the junction created by way of normal biologic healing of the anastomosis, eventually serving as a vascular access site for dialysis needle placement. However, due to underlying diseases in late stages, many patients present blood vessels that are non-viable for creation of a native AV fistula. In these patients, synthetic vascular grafts are implanted to create a shunt from the arterial side to the venous side of the circulatory system with the synthetic conduit serving as the location for vascular access. Expanded PTFE and cuffed double lumen silicone and urethane catheters are commonly used options for vascular access for hemodialysis with the latter being placed in a central venous site and the former typical implanted in the arm typically connecting a peripheral artery to a vein. E-PTFE grafts are preferred to central venous catheters because they perform better, although they are still far inferior to the preferred native fistulas.

The most common complication reported is low patency rates in ePTFE grafts, i.e., 50% at 1 year, and only 25% at 2 years (see *Vascular Access in Hemodialysis: Issues, Management, and Emerging Concepts*, Roy-Chaudhary et al., Cardiol Clin 23, 249-273 (2005) and FIG. 6, generally). Thus, only 1 in 4 patients with these synthetic grafts have unblocked (or patent) grafts at 2 years. The predominant source of this problem is that of neo-intimal hyperplasia, which occurs nearly 70% of the time at the venous anastomosis site of the graft, with the remainder of the graft blockages occurring at the arterial site or mid graft. Other complications include formation of pseudo-aneurysms in the graft (dilations), shredding of the graft wall due to repeated needle perforations, and thrombosis at needle perforations that do not close after needle removal. Secondarily, venous or arterial neo-intimal hyperplasia occurs due to the fact that the currently used ePTFE grafts are perceived by the host as a foreign body, eliciting an exuberant foreign body inflammatory response at the site of anastomosis, eventually resulting in hyperproliferation of cells that deposit undesirable tissue in the lumen of the graft or vein/artery at the anastomosis site or just downstream from the venous anastomosis location. In addition, current ePTFE conduits do not address compliance mismatch issues on the artery or venous side and clinicians point to this being another source of biological/ biomechanical mismatch that results in hyperplastic response that leads to reduced patency rates. Another reason for lack of patency is the inability of ePTFE grafts to form a viable endothelial cell lining on the inner lumen, which if formed would be the ideal biological interface between the graft and the blood flow. Formation of a viable endothelial layer that presents the appropriate anti-thrombotic receptor site proteins to the blood flow would represent an ideal solution for AV shunt grafts. Finally, needle access sites in ePTFE grafts for dialysis are commonly reported sites for graft failures which can range from lack of closure/healing, blood stream and graft site infection, formation of pseudo aneurysms, and destruction of the graft wall due to multiple perforations, all of which require graft removal and replacement. These problems occur primarily due to two reasons: (1) inability of ePTFE conduits to self-close needle perforation site, and (2) inability of ePTFE conduits to produce biologic healing at needle perforation sites. The ability of the graft wall materials to self-close would represent a step forward in terms of reducing the damage caused by needle perforation and would limit the various complications. However, the inability of the synthetic ePTFE graft to go through a normal wound healing process, similar to what happens during vascular access at a venous or arterial site is a huge drawback. Since current grafts do not allow for effective cellular infiltration, angiogenesis, and tissue integration, they function primarily as a passive conduit and are susceptible to perforation related pin holing failures. If the graft wall is engineered to completely biointegrate, then there is an opportunity for the cellular, vascular, and tissue components that are present as a composite structure within the graft wall to respond with a biological healing response starting with hemostasis, inflammation, proliferation, and tissue remodeling towards a healed puncture site. Thus there is an ongoing need for a synthetic, implantable construct that overcomes these and other deficiencies of the prior art.

SUMMARY OF THE INVENTION

The following provides a summary of certain exemplary embodiments of the present invention. This summary is not an extensive overview and is not intended to identify key or critical aspects or elements of the present invention or to delineate its scope.

In accordance with one aspect of the present invention, a first synthetic construct suitable for implantation into a biological organism is provided. This synthetic construct includes at least one polymer scaffold; wherein the at least one polymer scaffold includes at least one layer of polymer fibers that have been deposited by electrospinning; wherein the orientation of the fibers in the at least one polymer scaffold relative to one another is generally parallel, random, or both; and wherein the at least one polymer scaffold has been adapted to function as at least one of a substantially two-dimensional implantable structure and a substantially three-dimensional implantable tubular structure.

In accordance with another aspect of the present invention, a second synthetic construct suitable for implantation into a biological organism is provided. This synthetic construct includes at least one polymer scaffold; wherein the at least one polymer scaffold includes at least one layer of polymer fibers that have been deposited by electrospinning; wherein the orientation of the fibers in the at least one polymer scaffold relative to one another is generally parallel, random, or both; and wherein the at least one polymer scaffold is a substantially three-dimensional structure that is adapted for use as an arteriovenous shunt.

In yet another aspect of this invention, a third synthetic construct suitable for implantation into a biological organism is provided. This synthetic construct includes at least one polymer scaffold; wherein the at least one polymer scaffold includes at least one layer of polymer fibers that have been deposited by electrospinning; wherein the orientation of the fibers in the at least one polymer scaffold relative to one another is generally parallel, random, or both; and wherein the at least one polymer scaffold is a substantially three-dimensional structure that is adapted for use as a vascular implant; stent; graft; conduit; or combinations thereof.

Additional features and aspects of the present invention will become apparent to those of ordinary skill in the art upon reading and understanding the following detailed description of the exemplary embodiments. As will be appreciated by the skilled artisan, further embodiments of the invention are possible without departing from the scope and spirit of the invention. Accordingly, the Figures and associated descriptions are to be regarded as illustrative and not restrictive in nature.

DESCRIPTION OF THE FIGURES

The accompanying drawings, which are incorporated into and form a part of the specification, schematically illustrate one or more exemplary embodiments of the invention and, together with the general description given above and detailed description given below, serve to explain the principles of the invention, and wherein:

FIG. 7 is a table that provides measurements of puncture holes in different materials with a 17 gauge dialysis needle; Dacron and Goretex were used 'off the shelf' and PCL, PET, and PU were electrospun sheets;

FIG. 8 is a schematic representation of the effect of incorporating chitosan into an exemplary scaffold of this invention; and FIG. 9 includes a series of photographs depicting fluorescent nanodiamonds (left); a scanning electron micrograph of fibers with nanodiamonds (middle); and hiPSC-CMs stained with green sarcomeric α-actinin, blue nucleus and red fluorescent nanodiamonds to label the fibers (right).

DETAILED DESCRIPTION OF THE INVENTION

Figure 1:
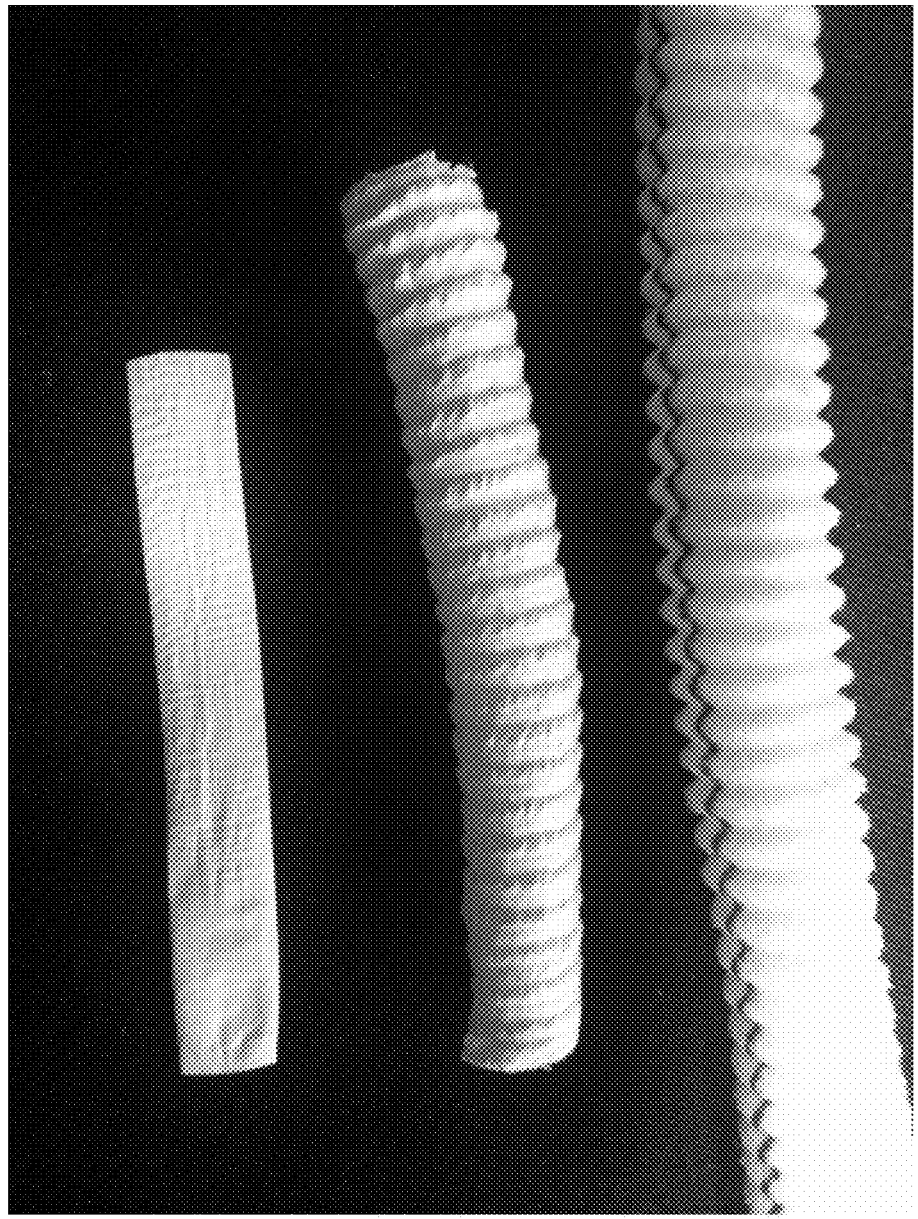
FIG. 1 is a photograph that depicts an electrospun tube (left); an electrospun tube with ridges (middle); and a Dacron vascular graft with ridges (right)

Exemplary embodiments of the present invention are now described with reference to the Figures. Although the following detailed description contains many specifics for purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed invention.

With reference generally to the Figures, the present invention involves the development and construction of implantable artificial organs and tissues for humans and/or animals, and more specifically to a process or method for manufacturing two and three-dimensional polymer microscale and nanoscale structures for use as scaffolds in the growth of biological structures such as hollow organs, luminal structures, and/or other structures within the body. The use of these scaffolds in creating or repairing numerous and multiple biological tissues and structures, e.g., the trachea, esophagus, small intestine, large intestine, duodenum, jejunum, cardiovascular tissues, bone, etc., is contemplated by and included in this invention. Exemplary versions of the manufacturing process of this invention include preparing a preform that is based on an actual native tissue and/or organ; electrospinning one or more layers of nanoscale (less than 1000 nanometers) or microscale (less than 50 microns) polymer fibers on the preform to form a nanofiber-based scaffold. The fibers are typically formed by electrospinning by extruding a polymer solution from a fiberization tip; creating an electronic field proximate to the fiberization tip; and positioning a ground or opposite polarity within the preform. The preform may be rotated to align the fibers on the preform or a second ground or polarity may be placed in the preform and rapidly switching the electric field to align the fibers. The microscale and nanoscale polymer fibers may be randomly aligned or maybe substantially parallel or both. These nanofiber structures may be seeded with one or more types of biological cells prior to implantation in the body to increase the rate of tissue growth into the scaffold. The polymer scaffold may include autologous cells or allogeneic cells, and wherein the autologous cells or allogeneic cells further include cord blood cells, platelets, embryonic stem cells, induced pluripotent cells, mesenchymal cells, placental cells, bone marrow derived cells, hematopoietic cells, epithelial cells, endothelial cells, smooth muscle cells, blood, blood plasma, platelet rich plasma, stromal vascular fraction, dental pulp, fibroblasts, or combinations thereof. These biological cells may be applied to the surface of the scaffold or distributed throughout the scaffold matrix utilizing perfusion within a bioreactor.

Choosing a material that accurately mimics the mechanical properties of the native tissue or organ may promote proper stem cell differentiation and facilitate normal function of the replacement tissue or organ. Included materials may be non-resorbable for permanent implantation or may be designed to slowly degrade while the host body rebuilds the native tissue. In the latter case, the implanted prosthesis will eventually be completely resorbed. Permanent (i.e., non-resorbable) polymers may include polyethylene, polyethylene oxide, polyethylene terephthalate, polyester, polymethylmethacrylate, polyacrylonitrile, silicone, polyurethane, polycarbonate, polyether ketone ketone, polyether ether ketone, polyether imide, polyamide, polystyrene, polyether sulfone, polysulfone, polyvinyl acetate, or combinations thereof. Degradable (resorbable) materials may include polycaprolactone (PCL); polylactic acid (PLA); polyglycolic acid (PGA); polydioxanone (PDO); Poly(3-hydroxybutyrate-co-3-hydroxyvalerate) (PHBV); trim ethylene carbonate (TMC); polydiols, gelatin, collagen, fibronectin, or combinations thereof. Fibers may be electrospun onto a preform with a desired prosthesis shape. An exemplary mandrel (preform) is coated with Teflon or similar material to facilitate removal of the scaffold after deposition or a slight taper (e.g., about 1°) can be manufactured into the mandrel. Nearly any size or shape can be produced from the electrospun fibers by using a pre-shaped form and the fiber deposition methods of the present invention.

Closely mimicking the structural aspects of the tissue or organ is important with regard to replicating the function of the native tissue or organ. By controlling the orientation of the fibers and assembling a composite structure of different materials and/or different fiber orientations it is possible to control and direct cell orientation and differentiation. Fiber orientation can be altered in each layer of a composite or sandwich scaffold in addition to the material and porosity to most closely mimic the native tissue. A properly constructed scaffold will permit substantially complete cellular penetration and uniform seeding for proper function and prevention of necrotic areas developing. If the fiber packing is too dense, then cells may not be able to penetrate or migrate from the exposed surfaces into the inner portions of the scaffold. However, if the fiber packing is not close enough, then attached cells may not be able to properly fill the voids, communicate and signal each other and a complete tissue or organ may not be developed. Controlling fiber diameter can be used to change scaffold porosity as the porosity scales with fiber diameter. Alternatively, blends of different polymers may be electrospun together and one polymer preferentially dissolved to increase scaffold porosity. The properties of the fibers can be controlled to optimize the fiber diameter, the fiber spacing or porosity, the morphology of each fiber such as the porosity of the fibers or the aspect ratio, varying the shape from round to ribbon-like. The precursor solution described below may be controlled to optimize the modulus or other mechanical properties of each fiber, the fiber composition, and/or the degradation rate (from rapidly biosoluable to biopersistent). The fibers may also be formed as drug eluting fibers, anti-bacterial fibers or the fibers may be conductive fibers, radio opaque fibers to aid in positioning or locating the fibers in an x-ray, CT or other scan.

In accordance with certain embodiments of this invention, the process of electrospinning is driven by the application of a high voltage, typically between 0 and 30 kV, to a droplet of a polymer solution or melt at a flow rate between 0 and 50 ml/h to create a condition of charge separation between two electrodes and within the polymer solution to produce a polymer jet. A typical polymer solution would consist of a polymer such as polycaprolactone, polystyrene, or polyethersulfone and a solvent such as 1,1,1,3,3,3-Hexafluoro-2-propanol, N,N-Dimethylformamide, acetone, or tetrahydrofuran in a concentration range of 1-50 wt %. As the jet of polymer solution travels toward the electrode it is elongated into small diameter fibers having a diameter of about 100 nm to 50 μm. The surfaces of the polymer fibers have been modified to include pores (having a size of about 100 nm to 250 μm), dimples, hairs, or combinations thereof In accordance with certain embodiments of this invention, an exemplary preparation of electrospinning solution typically includes polyethylene terephthalate (PET), polycaprolactone (PCL), polylactic acid (PLA), polyglycolic acid (PGA), polyetherketoneketone (PEKK), polyurethane (PU), polycarbonate (PC), polyamide (Nylon), natural polymers such as collagen; gelatin; fibrin; fibronectin; albumin; hyaluronic acid; elastin; or combinations thereof that are mixed with a solvent and dissolved. Suitable solvents include acetone; dimethylformamide; dimethylsulfoxide; N-Methylpyrrolidone; acetonitrile; hexanes; ether; dioxane; ethyl acetate; pyridine; toluene; xylene; tetrahydrofuran;

trifluoroacetic acid; trifluoroethanol; hexafluoroisopropanol; acetic acid; dimethylacetamide; chloroform; dichloromethane; formic acid; water; alcohols; ionic compounds; or combinations thereof. The electrospinning solution may further include additives selected from the group consisting of fluorescence compounds; radio opaque compounds; antibacterial compounds; anti-inflammatory compounds; growth hormones; conductive compounds; ceramic compounds; metallic compounds; cell growth promoting compounds; proteins; hormones; cytokines; and combinations thereof.

A substrate or form is typically prepared for the deposition of nanofibers. Optionally, simulated cartilage or other supportive tissue may be applied to the form and the fibers are then sprayed onto or transferred onto a form to build up the scaffold. While the present invention may be useful for the preparation of a number of bodily tissues, including hollow organs, three-dimensional structures within the body such as trachea, esophagus, intestine or luminal structures, such as nerves (epineurium or perineurium), veins and arteries (aorta, tunica externa, external elastic lamina, tunica medica, internal elastic lamina, tunica inima) the preparation of a human trachea is shown by example herein. Other preforms for species such as primates, cats, dogs, horses and cattle may be produced. The design of the implantable synthetic construct may also be based on a CAD model of a patient's actual relevant anatomy, wherein the CAD model has been derived from a CT scan or MRI of the relevant organ, tissue, or other native structure. U-shaped, branched, and spiral structures are also aspects of the present invention.

The effects of mechanical strain on electrospun polymer scaffolds has been described in the literature (see, *Microstructure-Property Relationships in a Tissue Engineering Scaffold*, Johnson et al., Journal of Applied Polymer Science, Vol. 104, 2919-2927 (2007) and *Quantitative Analysis of Complex Glioma Cell Migration on Electrospun Polycaprolcatone Using Time-Lapse Microscopy*, Johnson et al., Tissue Engineering; Part C, Volume 15, Number 4, 531-540 (2009), which are incorporated by reference herein, in their entirety, for all purposes. Strains as low as 10% appear to rearrange and align the fibers in the direction of loading. This alignment increases with the applied strain until over 60% of the fibers are aligned within ±10% of the direction of applied stress. If cells are present during fiber rearrangement in vivo or in vitro, they could conceivably be affected by these changes depending on the overall rate of strain. Fiber alignment is retained following a single cycle of extension and release. This has significant biological implications for a broad array of future tissue-engineering operations. As cells move across such a substrate, biased motion is likely as locomotion is based on forming and then dissolving a series of focal adhesions. Formation of these adhesions along the fiber direction may be easier than for fibers perpendicular to that direction although this will be partially controlled by the spacing between the fibers. This has longer-term consequences for the eventual control of the architecture of tissues that develop upon such substrates.

Cellular mobility parallel to the fiber direction means that it is possible to control and direct cell proliferation and migration by prestraining scaffolds to align the fibers in certain directions. This would create tailored structures with highly aligned fibers and, as a result, highly aligned cells. Of additional importance is the fact that many envisioned applications of tissue-engineering scaffolds will involve the use of cyclic stresses designed to achieve specific architectures in the biological component of the developing tissue. If the scaffold experiences continuing hysteresis in which orientation increases versus the number of cycles the efficiency of the overall process will be greatly enhanced. For blood vessels, as an example, the application of cyclic pressures will produce preferential stresses that could cause significant alignment of the fibers in the circumferential direction. This could cause cellular alignment in the circumferential direction, potentially creating a more biomimetic arrangement.

Cell seeding of these electrospun scaffolds can be accomplished through a variety of techniques, including (by way of example) vacuum seeding, perfusion seeding, or filtration seeding. Since the scaffolds are porous, the cells and culture media can be perfused through the scaffolds, thereby entrapping the cells and allowing the media to flow through. Any type of cell may be seeded into the scaffold, including (by way of example) autologous cells or allogeneic cells, and wherein the autologous cells or allogeneic cells further include cord blood cells, platelets, embryonic stem cells, induced pluripotent cells, mesenchymal cells, placental cells, bone marrow derived cells, hematopoietic cells, epithelial cells, endothelial cells, smooth muscle cells, blood, blood plasma, platelet rich plasma, stromal vascular fraction, dental pulp, fibroblasts, or combinations thereof. In some embodiments, the cells are added to the scaffold immediately before implantation into the patient, while in other embodiments, the cells are cultured for a predetermined time period (e.g. hours or days) on the scaffold before the implantation thereof into the patient. The polymer fibers of the scaffolds may also be coated, treated or impregnated with at least one compound that promotes cellular attachment to the scaffold and subsequent proliferation, angiogenesis, and tissue synthesis; or promotes engraftment of the scaffold into the biological organism. The least one compound may include proteins, peptides, growth factors, cytokines, antibiotics, anti-inflammatory agents, anti-neoplastic agents, or combinations thereof.

Exemplary embodiments and variants of the present invention include the following general features and/or aspects: (i) a composite scaffold seeded with stem cells and promoted to differentiate into stratified tissue; (ii) separate scaffold layers or sheets seeded independently to form different types of tissue and then assembled together using sutures, adhesive or welding to form a tubular shape and the stratified tissue; (iii) a scaffold implanted without cells for immediate replacement of damaged tissue and allow for cellular migration in vivo; (iv) an electrospun fiber scaffold made from non-resorbable materials such as polyethylene terephthalate, polyurethane, polycarbonate, poly ether ketone ketone; (v) an electrospun fiber scaffold made from resorbable materials such as polycaprolactone, polylactic acid, polyglycolic acid; (vi) an electrospun fiber scaffold made from natural polymers such as collagen, gelatin, fibronectin, hyaluronic acid; chitosan; alginate; or any combination of material types; (vii) an electrospun fiber scaffold made from a single layer of oriented fibers or a composite comprising layers of oriented fiber to correspond to the native structure and help orient and differentiate cells (fiber orientation can be from a rotating mandrel (circumferential fiber alignment), a translating mandrel (longitudinal fiber alignment), or split ground method of using electrostatics to align the fiber); (viii) using a pre-shaped mandrel or form to deposit fibers onto to achieve a near net shaped organs; and (ix) using a pre-shaped mandrel or form to deposit fibers onto to achieve a near net shaped segment/patch.

The polymer fiber scaffolds of the present invention may be used to manufacture two-dimensional biocompatible patches of varying thickness for use in humans or animals as an aid in wound healing involving muscles, internal organs, bones, cartilage, and/or external tissues. Biocompatible materials typically elicit little or no immune response in human or veterinary applications. In one or more exemplary embodiments, these patches include substantially parallel electrospun nanoscale and microscale polymer fibers. These patches may be seeded with biological cells prior to use to increase the rate of tissue growth into the patch. Such biological cells may include autologous or allergenic cells such as cord blood cells, embryonic stem cells, induced pluripotent cells, mesenchymal cells, placental cells, bone marrow derived cells, hematopoietic cells, epithelial cells, endothelial cells, fibroblasts and chondrocytes. Examples of internal uses include tissue, ocular tissue (lens, cornea, optic nerve or retina), intestinal tissue, internal organs such as the liver, kidney, spleen, pancreas, esophagus, trachea, uterus, stomach, bladder, muscles, tendons, ligaments, nerves, durra matter and other brain structures, dental structures, blood vessels and other bodily structures. Examples of external uses may include wound dressings, burn and abrasion coverings, and recovery aides to inhibit the formation of scar tissue. External structures are typically the skin but may include the cornea or surface of the eye, the ear canal, the mouth and nasal passages or the nail bed. In some embodiments, the patches of the present invention are modified to be electrically conductive.

Figure 2:
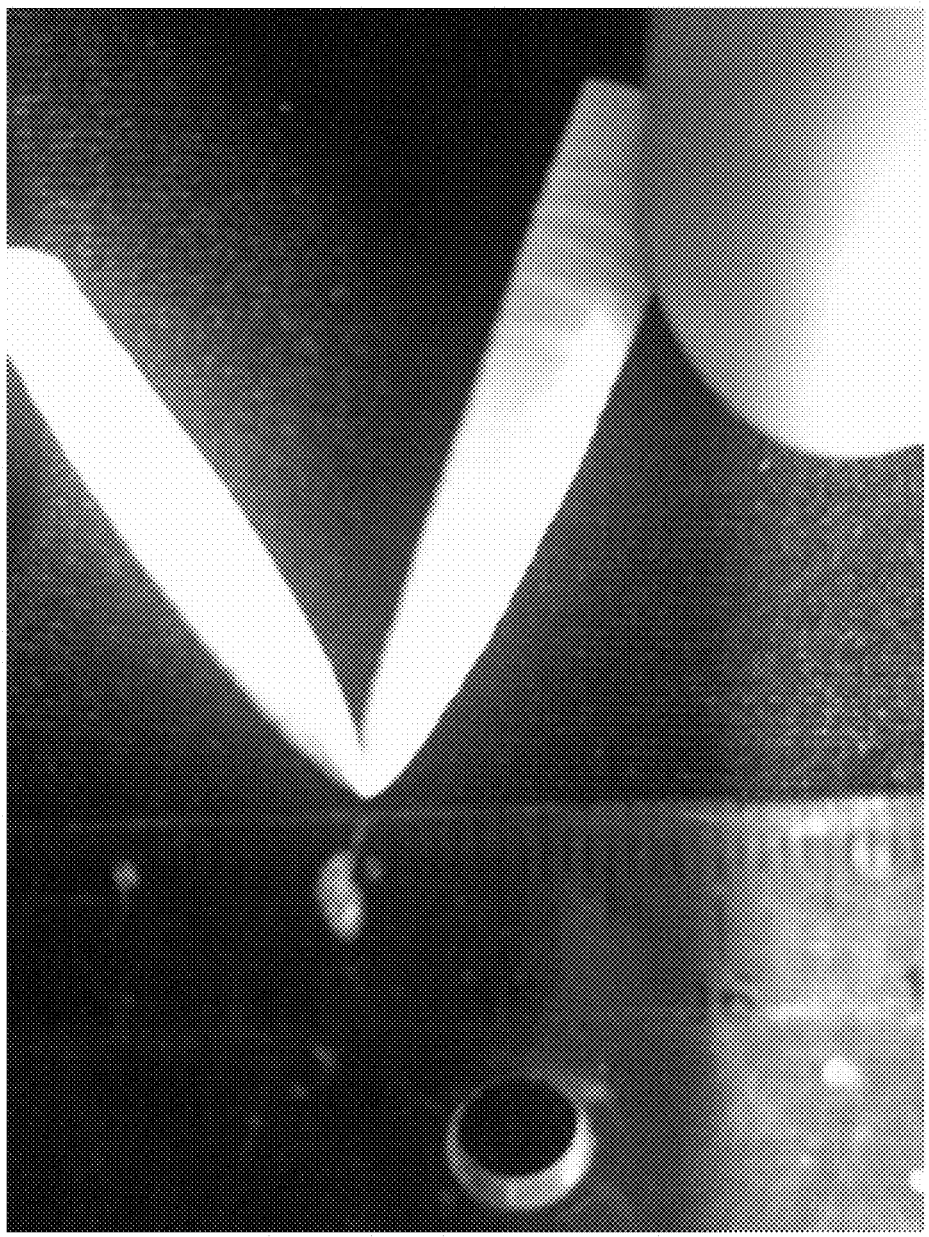
FIG. 2 is a photograph that depicts an electrospun PCL tube.
Figure 3:
FIG. 3 is a photograph that depicts an electrospun PCL tube with ridges.
Figure 4:
FIG. 4 is a photograph that depicts a Dacron vascular graft with ridges.
Figure 5:
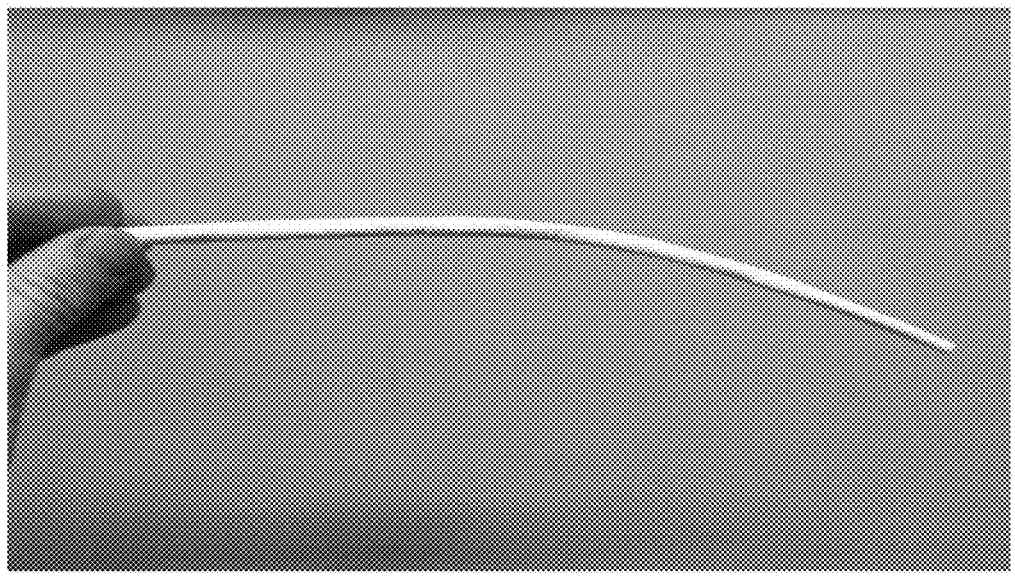
FIG. 5 is a photograph that depicts an electrospun graft wherein the material includes a gradient of PET on the left to PU on the right creating a gradient from stiff to elastic, respectively.
Figure 6:
FIG. 6 is a photograph that depicts a metallic vascular stent with electrospun fibers deposited directly onto the stent.

With regard to the creation of arteriovenous shunt grafts in accordance with the present invention, various solutions to the challenges described above are provided herein. The primary facilitating factor in achieving these solutions is the ability to design and manufacture tailored electrospun grafts that are manufactured from the nanometer or micrometer length scale to render specific properties in the graft wall through the thickness as well as along the length of the graft itself from the arterial side to the venous side. With reference to FIGS. 1-7, a first embodiment provides a Nan fibered graft material that is created using elastomeric fibers assembled in orientations that allow for complete or almost complete self-closure of the needle access site. This tailored Nan fibered graft material can be fabricated from a multitude of biocompatible biomaterials (polyurethane, polycaprolactone, polyethylene terephthalate, etc., or combinations thereof). A second embodiment provides a Nan fibered graft that contains macroscopic radial reinforcements or ridges to increase the kink resistance of the conduit, allowing it to be placed in a bent configuration without collapse of the lumen. An alternative approach to increasing kink resistance is to incorporate helically wound or spirally wound fiber reinforcements into the graft wall at the nano, micro, or macro length scales to mimic natural medial and adventitial collagen orientations. A third embodiment provides a graft that varies in compliance from the arterial side to the venous side in a manner as to reduce the mismatch in compliance between the sides through different fiber orientations; different materials; different graft thicknesses; different processing methods; or combinations thereof. A fourth embodiment encompasses the structure of all the previously described grafts at the nano or micro length scale wherein the outside surface of the graft and a certain percentage of the wall thickness (up to 90% of the wall from the outside in) are engineered with Nan fibered assemblies to mimic the extracellular matrix of a natural blood vessel or alternately to mimic the ECM of stromal tissue to induce maximal disintegration through the vessel wall, natural tissue stratification, and establish a confluent endothelial layer on the lumen. This unique feature addresses several issues including improved vessel to graft incorporation and biomechanical compliance matching, and self-healing of needle perforation sites by way of biologic wound repair mechanisms. Improved vessel to graft incorporation as the primary outcome is achieved by controlling and limiting the foreign body response to much lower levels than what is typically seen with current ePTFE grafts. A fifth embodiment relates to the luminal surface of all the above graft designs wherein the inner surface (intimal surface) of the Nan fibered graft is engineered using synthetic materials to replicate the ultra structure of the sub-intimal collage nous basement membrane typically found in native blood vessels. This nanostructure luminal surface promotes attachment of circulating cells and their phenotypic modification to endothelial cells following attachment to the luminal surface, thereby preventing thrombosis and noontime hyperplasia. In some embodiments (as described below) the arteriovenous shunt is electrically conductive, and in other embodiments, a hood-like structure is formed on one or both ends thereof.

Certain embodiments of the present invention are also useful for vascular implants; stents; grafts; conduits; or combinations thereof, some of which may include a hood-like structure formed on one or both ends thereof, and some of which are electrically conductive. Relatively low modulus polymers such as PCL, PET, PGLA, and PU may be included in the fiber scaffolds of this embodiment. Polymer fibers may be aligned in a circumferential direction to provide improved burst pressure strength and/or to align the endothelial cells on the lumen to mimic native vessels. Tri-layered tubes may be made using different fiber alignments, different polymers, and different porosities to mimic native vessels. A core/shell fiber structure may be utilized for providing an outer shell that is biocompatible and anti-thrombogenic while an inner core provides rigidity and mechanical strength. Drugs, antibiotics, growth factors, cytokines and other molecules may be embedded in the fibers for gradual time-release. Multiple polymers may be co-electrospun to produce individual fibers of each polymer or the polymers may be mixed in solution to produce fibers of mixed polymers. Sacrificial fibers or particles may be added that can be preferentially dissolved to create additional porosity throughout the scaffold.

With regard to the creation of tissue engineered vascular grafts, the fiber scaffolds of the present invention enhance biocompatibility and provide for controlled degradation of the constructs (post implantation), thereby permitting replacement of an implant with new natural vasculature. A significant benefit of these features is reduction or elimination of occlusion in the area(s) receiving the graft(s). The combination of water-soluble chitosan and polycaprolactone (in a ratio of 2% chitosan to 98% polycaprolactone, for example) results in a unique construct, the degradation of which can be controlled or at least predicted. In an exemplary embodiment, polycaprolactone (Mn 70,000-90,000, Lot# MKBB8278) and chitosan (Medium molecular weight, Lot#MKBH1108V) were purchased from Sigma Aldrich Co, LLC (Missouri, USA). 1,1,1,3,3,3-hexafluoroisopropanol (Lot#F13E) was purchased from Oakwood Products, Inc. (South Carolina, USA). Formic acid (98%, Lot#K41305364) and acetic acid (99.7%, Lot#51154) were purchased from EMD Chemicals, Inc. (New Jersey, USA). For electrospinning, 3-10 wt % polycaprolactone (PCL) was dissolved in 1,1,1,3,3,3-hexafluoroisopropanol (HFIP) via rigorous stirring by a magnetic stir bar for 24 hours. The solution was transferred into a 60 cc syringe capped with a 20 gauge blunt needle, and loaded into a syringe pump (Fisher). The syringe was dispensed at a flow rate of 5 mL/hr and a grounded target was set up at a distance of 15 cm. A mandrel with a 500 μm diameter was positioned between the needle and the target, set 13 cm from the needle tip and rotated at 5000 RPM. To begin electrospinning, a +10 kV charge was applied to the syringe tip. All scaffolds were spun to a 150 μm wall thickness. To create PCL/CS blended grafts, 3-10 wt % PCL and 1-50 wt % chitosan (CS) relative to PCL was dissolved in a 7:3 w/w solution of formic acid (FA) and acetic acid (AA) and stirred via a magnetic stir bar for 3 hours. This solution was electrospun onto a low speed mandrel. The PCL/CS solution was dispensed at a flow rate of 0.1-10 mL/hr and a grounded mandrel was positioned 10 cm from the needle tip and rotated at 30 RPM. A +25 kV charge was applied to the syringe tip and electrospun to create a 150 μm wall thickness. Electrospinning the 3-10 wt % PCL+HFIP solution was also performed onto the slow speed mandrel using the same set up as the PCL/CS solution. The solution was dispensed at 5 mL/hr and electrospun at +12 kV onto a grounded mandrel to a wall thickness of 150 μm.

Research has indicated that it is possible to achieve about a 50% loss in ultimate tensile strength (UTS) in 2 weeks of in vitro degradation by incorporating chitosan. A desirable decrease in strain to failure and tensile strength indicates that the chitosan is accelerating the degradation of the nanofiber scaffolds. FIG. 8 provides a graphic representation of the effect of incorporating chitosan into an exemplary scaffold and lists some important benefits of including chitosan into the scaffold. Pure polycaprolactone (PCL) takes approximately 1 year to degrade in vivo, but by incorporating chitosan (CS) it is possible to tailor scaffold degradation from 4 weeks to 1 year based on the amount of CS. PCL lacks integrin binding sites for cell attachment; however, CS provides integrin binding sites. Because CS degrades rapidly, it creates additional porosity which facilitates cellular penetration into the scaffold and CS has well documented benefits including anti-inflammatory and anti-bacterial properties. FIG. 8 illustrates a combination of PCL+chitosan; however, it is also possible to blend chitosan into any synthetic or natural polymer to increase biocompatibility, anti-bacterial properties, and increase degradation rate. Chitosan can be difficult to electrospin effectively, so solvent blends are used that may include specifically HFIP, acetic acid (AA) and formic acid (AA), trifluoroethanol (TFE), trifluoroacetic acid (TFA), chloroform, dichloromethane (DCM), acetone, ethanol and methyl ether ketone (MEK).

Advantageously, it is possible to tailor or "tune" the mechanical properties of the constructs of the present invention by controlling the rotational speed of the mandrel/tube used in the electrospinning fiber deposition process. Essentially, rotational speed controls the radial stiffness of the resultant construct. The faster the rotational speed, the greater the degree of fiber alignment and overall stiffness, thereby increasing burst pressure strength and decreasing compliance. Native artery and vein data obtained through experimentation illustrate that it is possible to accurately reproduce grafts for both AV shunt applications and tissue engineered vascular graft applications using this approach.

Cells and tissues in the human body utilize electrical impulses to function (e.g., heart and skeletal muscle and nerve transmission). Healthy cells and tissue typically have a conductivity of approximately 0.16 S/m. Accordingly, synthetic scaffolds being implanted in the body may benefit from being conductive to facilitate cellular interaction. In one embodiment of the present invention, 50 nm nanodiamonds (NDs) that are both permanently fluorescent and electrically conductive have been embedded into an aligned nanofiber scaffold (see FIG. 9) for improving electrical conductivity across the scaffold, which may be an implantable patch or other structure. These embedded items are believed to improve the conduction velocity, excitation-contraction coupling (EC) of the cardiomyocytes on the patch, and the overall contractile kinetics of the patch. The biomimetic technology of these conductive nanofiber scaffolds provide a novel tissue engineered construct that, presumably, will improve cell migration and wound healing. NDs are mass produced and routinely used for industrial drilling and grinding applications, but more recently have been used for composites and thin film applications due to their demonstrated electrical conductivity. In addition to making the scaffold conductive, the NDs offer additional functionality to the patch, including long term in vivo fluorescence tracking, magnetic resonance imaging (MRI) contrast, and drug delivery. In still other embodiments of this invention, electrical conductivity is conferred to synthetic scaffolds by incorporating carbon nanotubes (CNT) or polyaniline (PANI) therein.

To make the fibers of the synthetic scaffolds of the present invention electrically conductive, one or more conductive materials are introduced into the polymer solution prior to beginning the process of electrospinning Typically, conductive materials have poor mechanical properties for use in tissue engineering constructs. However, once the percolation threshold is reached by the addition of a sufficient concentration of conductive material (ranging from about 0.01 wt % to about 10 wt %) to another material which is non-conductive, adequate mechanical properties can be maintained while making the scaffold electrically conductive. FIG. 9 includes a series of photographs depicting fluorescent nanodiamonds (left); a scanning electron micrograph of fibers with nanodiamonds (middle); and hiPSC-CMs stained with green sarcomeric a-actinin, blue nucleus and red fluorescent nanodiamonds to label the fibers (right). The concentration of 50 nm diamonds used is sufficiently high as to cause the entire nanofibers to fluoresce.

While the present invention has been illustrated by the description of exemplary embodiments thereof, and while the embodiments have been described in certain detail, it is not the intention of the Applicant to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the applicant's general inventive concept.

What is claimed:

1. A scaffold consisting of:
   a layer of biocompatible electrospun polymer fibers having an orientation relative to one another that is generally parallel, random, or a combination thereof;
   the scaffold having a shape selected from the group consisting of an arteriovenous shunt, a vascular implant, a stent, a conduit, and combinations thereof.

2. The scaffold of claim 1, wherein the biocompatible electrospun polymer fibers comprise a non-resorbable material selected from the group consisting of polyethylene, polyethylene oxide, polyethylene terephthalate, polyester, polymethylmethacrylate, polyacrylonitrile, silicone, polyurethane, polycarbonate, polyether ketone ketone, polyether ether ketone, polyether imide, polyamide, polystyrene, polyether sulfone, polysulfone, polyvinyl acetate, and combinations thereof.

3. The scaffold of claim 1, wherein the biocompatible electrospun polymer fibers comprise a resorbable material selected from the group consisting of polycaprolactone (PCL); polylactic acid (PLA); polyglycolic acid (PGA); polydioxanone (PDO); Poly(3- hydroxybutyrate-co-3-hydroxyvalerate) (PHBV); trimethylene carbonate (TMC); polydiols; and combinations thereof.

4. The scaffold of claim 1, wherein the biocompatible electrospun polymer fibers comprise a natural polymer selected from the group consisting of collagen; gelatin; fibrin; fibronectin; albumin; hyaluronic acid; elastin; chitosan; alginate; and combinations thereof.

5. The scaffold of claim 1, wherein the biocompatible electrospun polymer fibers have a diameter of about 100 nm to 50 μm and a pore size of about 100 nm to 250 μm.

6. The scaffold of claim 1, wherein a surface of the biocompatible electrospun polymer fibers comprise features selected from the group consisting of pores, dimples, hairs, and combinations thereof.

7. A scaffold consisting of:
a layer of biocompatible electrospun polymer fibers having an orientation relative to one another is generally parallel, random, or a combination thereof;
the scaffold having a uniform thickness and a shape of an arteriovenous shunt;
wherein the scaffold varies in compliance from an arterial side to a venous side.

8. The scaffold of claim 7, wherein the biocompatible electrospun polymer fibers comprise an elastomeric material selected from the group consisting of polyurethane; polycaprolactone; polyethylene terephthalate; polydioxanone; chitosan; and combinations thereof.

9. The scaffold of claim 7, wherein the arteriovenous shunt is electrically conductive.

10. The scaffold of claim 7, wherein the arteriovenous shunt has been modeled on actual patient anatomy.

11. The scaffold of claim 1, having an increased degree of fiber alignment configured to increase burst pressure strength and decrease compliance.

* * * * *